(12) United States Patent
Graziano et al.

(10) Patent No.: US 9,039,177 B2
(45) Date of Patent: May 26, 2015

(54) EYE IMAGE AND VIDEO CAPTURE SYSTEM AND ASSOCIATED METHODS

(75) Inventors: Jeremy Graziano, Portland, OR (US); Martin Waugh, Portland, OR (US)

(73) Assignee: EYE PHOTO SYSTEMS, INC., Portland, OR (US)

( * ) Notice: Subject to any disclaimer, the term of this patent is extended or adjusted under 35 U.S.C. 154(b) by 61 days.

(21) Appl. No.: 13/703,330

(22) PCT Filed: Jun. 10, 2011

(86) PCT No.: PCT/US2011/040109
§ 371 (c)(1),
(2), (4) Date: Dec. 10, 2012

(87) PCT Pub. No.: WO2011/156797
PCT Pub. Date: Dec. 15, 2011

(65) Prior Publication Data
US 2013/0088686 A1    Apr. 11, 2013

Related U.S. Application Data

(60) Provisional application No. 61/353,542, filed on Jun. 10, 2010.

(51) Int. Cl.
*A61B 3/14* (2006.01)
*A61B 3/10* (2006.01)
*A61B 3/00* (2006.01)

(52) U.S. Cl.
CPC ............ *A61B 3/14* (2013.01); *A61B 3/0025* (2013.01); *A61B 3/0041* (2013.01); *A61B 3/0008* (2013.01); *A61B 3/145* (2013.01); *A61B 3/0033* (2013.01)

(58) Field of Classification Search
CPC .. A61B 3/0041; A61B 3/0025; A61B 3/0033; A61B 3/0008; A61B 3/14; A61B 3/145
USPC .......................................... 351/206, 246, 221
See application file for complete search history.

(56) References Cited

U.S. PATENT DOCUMENTS 5,557,321 A  *  9/1996  Kohayakawa et al. .......... 348/78
5,943,116 A       8/1999  Zeimer
6,585,374 B2 *  7/2003  Matsumoto .................... 351/206

(Continued)

OTHER PUBLICATIONS

Instruction Manual for RS-1000 Zoom Slitlamp, Righton, Right Group, Aug. 2004, 91 pages.

*Primary Examiner* — Thomas K Pham
*Assistant Examiner* — Nicholas Pasko
(74) *Attorney, Agent, or Firm* — Marger Johnson & McCollom PC

(57) ABSTRACT

An eye image and video capture system (100) that includes at least one user interface from which a user may select one of a plurality of regions of an eye to image, each of the plurality of regions preferably having at least one correlated preset value for the light control components of the optics assembly and/or at least one correlated preset value for controlling the camera. A method associated with the eye image and video capture system. A slit lamp data detection system in which the slit lamp (200) preferably has a movable component that preferably has a direct relation to desired data. The slit lamp data detection system may be a slit lamp magnification data detection system for detecting magnification data. The slit lamp data detection system may be a slit lamp position data detection system for detecting position data that indicates which eye is being examined.

25 Claims, 12 Drawing Sheets

(56) References Cited

U.S. PATENT DOCUMENTS

| | | | |
|---|---|---|---|
| 7,300,154 B2 * | 11/2007 | Ono | 351/206 |
| 7,566,130 B2 * | 7/2009 | Okinishi | 351/206 |
| 7,905,598 B2 * | 3/2011 | Kishida et al. | 351/206 |
| 2006/0274269 A1 | 12/2006 | Koest | |
| 2008/0137034 A1 | 6/2008 | Wernick et al. | |
| 2009/0079937 A1 * | 3/2009 | Chen et al. | 351/210 |
| 2010/0110172 A1 * | 5/2010 | Satake | 348/78 |

* cited by examiner

EYE IMAGE AND VIDEO CAPTURE SYSTEM AND ASSOCIATED METHODS The present application is an application claiming the benefit of U.S. Provisional Patent Application Ser. No. 61/353,542, filed Jun. 10, 2010 and entitled "Eye Image And Video Capture System And Associated Methods." The present application is based on and claims priority from this application, the disclosure of which is hereby expressly incorporated herein by reference in its entirety.

BACKGROUND OF INVENTION

Described herein are systems for capturing images and video of eyes, and methods associated with such systems.

A slit lamp is an instrument used by doctors (for example, ophthalmologists and optometrists) to examine a patient's eyes. A slit lamp includes a high-intensity light source that can be focused to shine a thin slit of light into an eye of the patient and a low-power microscope that magnifies an image of the eye being examined.

Conventional systems for capturing images or video of a patient's eye that are usable with slit lamps fall into one of two categories: video capture and image capture.

The first category is a video capture system that records video of the patient's eye using, for example, a digital video camera. There are several disadvantages to conventional video capture systems when used to capture still images. First, a flash cannot be used. This means high magnification shots are essentially impossible, as miniscule movements at high magnification produce substantial blur. Second, extremely high levels of light are required to get a good image, and such levels can be uncomfortable to the patient. Third, video capture systems typically capture low resolution video. One particular conventional video capture system markets an ability to capture images. In reality, however, this video capture system merely provides a user with a series of images surrounding an image capture time, and requires the user to select a particular image to use. This approach not only provides the user with multiple inferior images, but also increases the amount of time necessary to obtain an image of a particular region of the eye.

The second category is an image capture system that captures images of the patient's eye using, for example, a digital single lens reflex (SLR) camera. Conventional image capture systems have the capability to capture higher resolution and thus higher quality images than conventional video capture systems. Conventional image capture systems, however, can also have drawbacks. For example, certain conventional image capture systems cannot capture video. As another example, certain conventional image capture systems require all of the light to be directed to the digital SLR camera when the image capture system is in use. This leaves no light for the slit lamp microscope and renders it impossible for the user to examine the patient's eyes while using the image capture system. Another disadvantage is that conventional image capture systems require the user to manually adjust a variable aperture during photo taking sessions and to know proper ISO (e.g. ISO standard 12232:2006 which is a system used to measure the sensitivity of digital imaging systems), flash, and variable aperture settings for the extensive variations of eye regions and for varying levels of magnification. These requirements can cause the user to devote time to adjusting settings during a patient examination, and/or can distract the user from the examination.

References that discuss slit lamps and/or capturing video images of all or part of an eye are disclosed in U.S. Pat. No. 4,175,839 to Muller et al., U.S. Pat. No. 4,331,392 to Sato, U.S. Pat. No. 4,767,204 to Blaha, U.S. Pat. No. 5,000,560 to Papritz et al., U.S. Pat. No. 5,196,874 to Muller et al., U.S. Pat. No. 5,424,788 to Satake et al., U.S. Pat. No. 5,757,461 to Kasahara et al., U.S. Pat. No. 7,311,401 to Goldfain et al., and U.S. Pat. No. 7,410,257 to Takeda. These references are herein incorporated by reference in their entirety.

BRIEF SUMMARY OF THE INVENTION

Described herein is an eye image and video capture system including a computing system, an optics controller, an optics assembly preferably has at least one adjustable light control component, a camera, and a flash assembly. The computing system has a system controller preferably has a series of instructions that cause the system to: (a) provide at least one user interface from which a user may select one of a plurality of regions of an eye to image, each of the plurality of regions preferably has at least one correlated preset value for the light control components of the optics assembly, each of the plurality of regions preferably has at least one correlated preset value for controlling the camera; (b) provide at least one user interface from which a user may select to cause the camera to selectively capture at least one image or capture at least one video; (c) receive a user selection of one of the plurality of regions of an eye to image; (d) receive a user selection of either causing the camera to capture at least one image or causing the camera to capture at least one video; (e) transmit at least one optics controller command for adjusting the at least one adjustable light control component of the optics assembly according to the at least one preset value correlated with the user selection of one of the plurality of regions of an eye to image; (f) transmit at least one camera controller command for controlling the camera according to the at least one preset value correlated with the user selection of one of the plurality of regions of an eye to image; and (g) transmit at least one camera actuating command for controlling the camera according to the user selection of one of the causing the camera to capture at least one image or causing the camera to capture at least one video.

In some preferred eye image and video capture systems, the computing system preferably has at least one memory and the system controller is stored on the at least one memory. In some preferred eye image and video capture systems, the computing system preferably has at least one processing unit, the at least one processing unit for executing the series of instructions.

In some preferred eye image and video capture systems, the system controller preferably has a series of instructions that cause the system to transmit the optics controller commands for adjusting the at least one adjustable light control component according to the at least one preset value correlated with the user selection of one of the plurality of regions of an eye to image via the optics controller to the at least one adjustable light control component. Alternatively, in some preferred eye image and video capture systems, the system controller preferably has a series of instructions that cause the system to transmit the optics controller commands for adjusting the at least one adjustable light control component according to the at least one preset value correlated with the user selection of one of the plurality of regions of an eye to image via the optics controller, the optics controller receiving the optics controller commands from the system, the optics controller transmitting the optics controller commands to the at least one adjustable light control component.

In some preferred eye image and video capture systems, the system controller preferably has at least one instruction that causes the system to transmit commands for actuating a flash. Alternatively, in some preferred eye image and video capture systems, the system controller preferably has at least one instruction that causes the system to transmit commands via the camera for actuating a flash.

In some preferred eye image and video capture systems, the system controller preferably has at least one instruction that causes the system to receive at least one captured image from the camera. Further, in some preferred eye image and video capture systems, the system controller preferably has at least one instruction that causes the system to display the at least one captured image.

In some preferred eye image and video capture systems, the system controller preferably has at least one instruction that causes the system to receive at least one captured video from the camera. Further, in some preferred eye image and video capture systems, the system controller preferably has at least one instruction that causes the system to display the at least one captured video.

Described herein is a method for capturing an image or a video using an eye image and video capture system. The eye image and video capture system preferably includes a computing system, an optics controller, an optics assembly preferably has at least one adjustable light control component, a camera, and a flash assembly. The method preferably includes the steps of: (a) providing at least one user interface from which a user may select one of a plurality of regions of an eye to image, each of the plurality of regions preferably has at least one correlated preset value for the light control components of the optics assembly, each of the plurality of regions preferably has at least one correlated preset value for controlling the camera; (b) providing at least one user interface from which a user may select to cause the camera to selectively capture at least one image or capture at least one video; (c) receiving a user selection of one of the plurality of regions of an eye to image; (d) receiving a user selection of either causing the camera to capture at least one image or causing the camera to capture at least one video; (e) transmitting commands for adjusting the at least one adjustable light control component of the optics assembly according to the at least one preset value correlated with the user selection of one of the plurality of regions of an eye to image; (f) transmitting commands for controlling the camera according to the at least one preset value correlated with the user selection of one of the plurality of regions of an eye to image; and (g) transmitting commands for controlling the camera according to the user selection of one of the causing the camera to capture at least one image or causing the camera to capture at least one video.

Some preferred methods for capturing an image or a video preferably includes the step of controlling the steps using a system controller stored in memory of the computing system. Some preferred methods for capturing an image or a video preferably includes the step of executing the steps using a processing unit of the computing system.

Some preferred methods for capturing an image or a video preferably includes the step of transmitting the optics controller commands for adjusting the at least one adjustable light control component according to the at least one preset value correlated with the user selection of one of the plurality of regions of an eye to image via the optics controller to the at least one adjustable light control component.

Some preferred methods for capturing an image or a video preferably includes the step of transmitting the optics controller commands for adjusting the at least one adjustable light control component according to the at least one preset value correlated with the user selection of one of the plurality of regions of an eye to image via the optics controller, the optics controller receiving the optics controller commands from the system, the optics controller transmitting the optics controller commands to the at least one adjustable light control component.

Some preferred methods for capturing an image or a video preferably includes the step of transmitting commands for actuating a flash. Alternatively, some preferred methods for capturing an image or a video preferably includes the step of transmitting commands via the camera for actuating a flash.

Some preferred methods for capturing an image or a video preferably includes the step of receiving at least one captured image from the camera. Further, some preferred methods for capturing an image or a video preferably includes the step of displaying the at least one captured image.

Some preferred methods for capturing an image or a video preferably includes the step of receiving at least one captured video from the camera. Further some preferred methods for capturing an image or a video preferably includes the step of displaying the at least one captured video.

Described herein is a slit lamp data detection system for use with a slit lamp and a system for capturing images or video of a patient's eye. The slit lamp preferably has a movable component that preferably has a direct relation to desired data. The slit lamp preferably has an associated stationary component. The system for capturing images or video of a patient's eye preferably has a computing system with a system controller. The slit lamp data detection system preferably includes: (a) a first part of a position indicator/detector system associated with the movable component of the slit lamp; (b) a second part of the position indicator/detector system associated with the stationary component associated with the slit lamp; and (c) the position indicator/detector system for gauging the relationship between the first part and the second part and transmitting relationship data to the system controller, the desired data being determinable from the relationship data.

For some preferred slit lamp data detection systems the slit lamp data detection system is a slit lamp magnification data detection system and the desired data is magnification data. Further, for some preferred slit lamp data detection systems the slit lamp data detection system is a slit lamp magnification data detection system and the desired data is magnification data, and the slit lamp magnification data detection system preferably includes: (a) a first part of a position indicator/detector system associated with an adjustable magnification control of the slit lamp; (b) a second part of the position indicator/detector system associated with the stationary component associated with the slit lamp; and (c) the position indicator/detector system for gauging the distance or angle relationship between the first part and the second part and transmitting distance or angle relationship data to the system controller, the magnification data being determinable from the distance or angle relationship data.

For some preferred slit lamp data detection systems the slit lamp data detection system is a slit lamp position data detection system and the desired data is position data that indicates which eye is being examined. Further, for some preferred slit lamp data detection systems the slit lamp data detection system is a slit lamp position data detection system and the desired data is position data that indicates which eye is being examined, and the slit lamp position data detection system preferably includes: (a) a first part of a position indicator/detector system associated with an adjustable magnification control of the slit lamp; (b) a second part of the position indicator/detector system associated with the stationary component associated with the slit lamp; and the position indicator/detector system for gauging the distance, angle, or presence/absence relationship between the first part and the second part and transmitting distance, angle, or presence/absence relationship data to the system controller, the position data being determinable from the distance, angle, or presence/absence relationship data.

Some preferred slit lamp data detection systems preferably include a system for capturing images or video of a patient's eye preferably has associated memory, the relationship data transmitted to the system controller being stored in the memory. Further, some preferred slit lamp data detection systems preferably include a system for capturing images or video of a patient's eye preferably has associated memory, the relationship data transmitted to the system controller being stored in the memory with associated captured images or video.

The foregoing and other objectives, features, combinations, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

The accompanying drawings illustrate an exemplary preferred eye image and video capture system and/or provide teachings by which the exemplary preferred eye image and video capture system are more readily understood.

Figure 1:
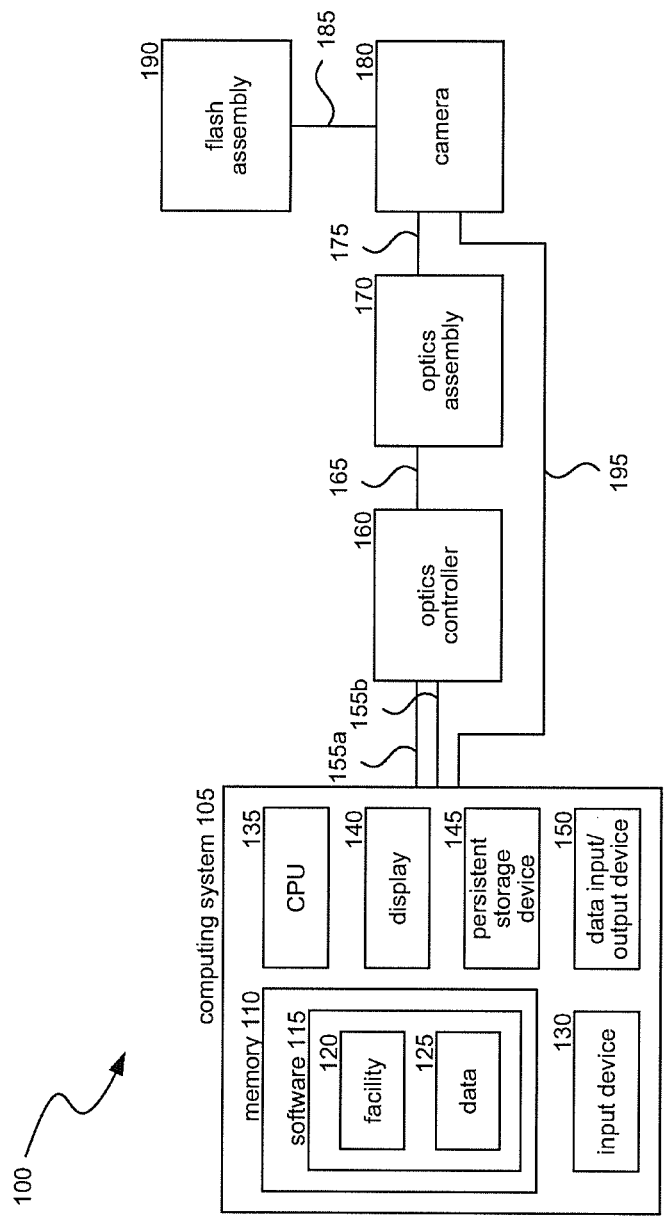
FIG. 1 is a block diagram illustrating an exemplary preferred eye image and video capture system configured in accordance with a preferred eye image and video capture system.

The drawing figures are not necessarily to scale. Certain features or components herein may be shown in somewhat schematic form and some details of conventional elements may not be shown or described in the interest of clarity and conciseness. The drawing figures are hereby incorporated in and constitute a part of this specification.

DETAILED DESCRIPTION OF THE INVENTION

Described herein is an eye image and video capture system that captures images and video of eyes and overcomes the problems discussed in the Background, as well as additional benefits. Overall, the examples herein of some prior or related systems and their limitations are intended to be illustrative and not exclusive. Other limitations of existing or prior systems will become apparent to those of skill in the art.

Described herein is an eye image and video capture system that preferably includes a computing system, an optics controller, an optics assembly, a camera, and a flash assembly. (Although shown as separate components, some of these elements may be combined in a single component. Alternatively, some of the functionality may be divided into multiple components.) The optics assembly is preferably configured to be functionally coupled between a magnification portion and an ocular portion of a slit lamp. The camera is preferably configured to be functionally coupled to the optics assembly. The optics assembly includes at least one adjustable light control component (which can be one of the shown as a rotatable beam splitter and a variable aperture) that can transmit at least some portion of the light exiting the magnification portion of the slit lamp toward the camera. The optics assembly also includes at least one electronic and/or electrical adjustment component (e.g. servo motors or other mechanisms that can create motion in response to a signal) that adjust the light control components according to commands (e.g. optics controller commands) issued by the computing system. The camera is operably coupled to the flash assembly and can cause the flash assembly to actuate when the camera is capturing an image. The computing system includes a software program (referred to herein as a "system controller" or "facility") that provides interfaces (shown as windows or screens represented on a computer display) that can be used to cause the camera to capture images and/or video. The system controller can allow a user to select at least one of a plurality of regions of the eye to image, each of which can have at least one correlated preset values or settings for the camera and/or at least one correlated preset values or settings for the at least one adjustable light control component of the optics assembly. When the user selects a region of the eye to image, the system controller can transmit to the optics controller commands for adjusting at least one adjustable light control component of the optics assembly according to the preset values. The optics controller receives such optics controller commands and, in turn, transmits corresponding commands for adjusting at least one adjustable light control component using at least one electronic and/or electrical adjustment component. The system controller can also transmit commands (e.g. camera controller commands and camera actuating commands) for controlling the camera to the camera according to the preset values. When the system controller receives an instruction (for example, from the user who actuates the system) to capture an image or video, the system controller transmits a corresponding command to the camera. The camera captures an image or video. The flash may also be actuated. The camera transmits the captured image or video to the system controller, which can display the captured image or video for the user to review and/or store the captured image or video for later review.

DEFINITIONS

Please note that the terms and phrases may have additional definitions and/or examples throughout the specification. Where otherwise not specifically defined, words, phrases, and acronyms are given their ordinary meaning in the art. The following paragraphs set forth some of the definitions for terms and phrases used herein.

- A "slit lamp" is an instrument used by doctors and other medical personnel to examine a patient's eyes that includes a high-intensity light source that can be focused to shine a thin slit of light into an eye of the patient and a low-power microscope that magnifies an image of the eye being examined.
- A "camera" is any camera that is controllable via an interface (e.g. a USB interface) by a computing system. Exemplary cameras include many digital cameras and/or SLR cameras.
- The "optics assembly" can be generally defined as a lens assembly for the camera to be used with the system described herein (including a slit lamp). The optics assembly has a variable aperture.
- The term "exposure setting" is a combination of ISO, flash power, and aperture size.
- The term "user" is meant to include doctors (e.g. ophthalmologists and optometrists) and other medical (including health care) personnel (including assistants and technicians).
- The term "system controller" (also referred to as the "facility") is preferably a software program preferably stored in non-transitory memory. The system controller directs steps of methods performed by elements of the an eye image and video capture system 100 including, but not limited to the computing system 105, the optics controller 160, the optics assembly 170, the camera 180, and/or the flash assembly 190. Because the system controller (shown as facility 120) directs operations, the steps in which components controlled by the system controller actually perform the specified function are may be attributed to the system controller. For example, although the data input/output device 140 may actually transmit commands, because the system controller directs the transmission of the commands, this step may be discussed as the system controller transmitting commands. Similarly, although the display 140 may actually display the captured image or video, because the system controller directs the display the captured image or video, this step may be discussed as the system controller displaying the captured image or video.
- The term "associated" is defined to mean integral or original, retrofitted, attached, positioned near, and/or functionally connected. For example, if a camera (or other component) is associated with an optics assembly (or other technology), the camera may be an original camera dedicated to the optics assembly, a camera that has been retrofitted into the optics assembly, an attached camera that is attached to the optics assembly, and/or a nearby camera that is positioned near the optics assembly. Depending on the context, the term "associated" may also mean "part of" or "related to." The terms "functionally" and "operatively" include connections that are not necessarily physical connections and/or direct connections. Connections shown as physical connections or direct connections may also be implemented as, for example, wireless and/or indirect connections (e.g. via intermediate elements).
- The terms "computing system" and "computer" are defined as devices capable of executing instructions or steps and may be implemented as a programmable logic device or other type of programmable apparatus known or yet to be discovered. The computing system and computer may be or may have an associated processing unit and/or associated memory. The processing unit may be a CPU, processor, microprocessor, controller, microcontroller, digital signal processor (DSP), integrated circuit (ASIC), a field programmable gate array signal (FPGA), state machine, and/or other programmable logic device programmable logic device, discrete gate or transistor logic, discrete hardware components, or any combination thereof designed to perform the functions described herein. The computing system and computer may be implemented using a general purpose computing system. Although shown as single units (e.g. CPU 135), it should be noted that the processing units may be implemented as multiple separate processing units. Similarly, multiple processors may be combined.
    - The term "memory" is defined to include any type of computer (or other technology)-readable media (also referred to as machine-readable storage medium) including, but not limited to attached storage media (e.g. hard disk drives, network disk drives, servers), internal storage media (e.g. RAM, ROM, EPROM, FLASH-EPROM, or any other memory chip or cartridge), removable storage media (e.g. CDs, DVDs, flash drives, memory cards, floppy disks, flexible disks), firmware, and/or other storage media known or yet to be discovered. Depending on its purpose, the memory may be transitory and/or non-transitory. For example, programs and subprograms are generally stored in non-transitory memory. Although shown as single units, it should be noted that the memories may be implemented as multiple separate memories. Similarly, multiple memories may be combined.
    - It should be noted that the terms "programs" and "subprograms" are defined as a series of instructions that may be implemented as software (i.e. computer program instructions or computer-readable program code) that may be loaded onto a computer to produce a machine, such that the instructions that execute on the computer create structures for implementing the functions described herein or shown in the figures. (For example, a system controller may be a program or subprogram that has a series of instructions loaded onto a computer or a memory associated therewith.) Alternatively, the "programs" and "subprograms" may be implemented in alternative forms (e.g. firmware and hardware) that are able achieve their respective function. Programs and subprograms implemented as software may be loaded onto a computer so that they can direct the computer to function in a particular manner, such that the instructions produce an article of manufacture including instruction structures that implement the function specified in the flow chart block or blocks. The programs and subprograms may also be loaded onto a computer to cause a series of operational steps to be performed on or by the computer to produce a computer implemented process such that the instructions that execute on the computer provide steps for implementing the functions specified in the flow chart block or blocks. The phrase "loaded onto a computer" also includes being loaded into the memory of the computer or a memory associated with or accessible by the computer. The shown programs and subprograms may be divided into multiple modules or may be combined. Software programs described herein (e.g. the "system controller" or the "facility") may be implemented as a program or a subprogram.

The terms "provide" and "providing" (and variations thereof) are meant to include generating and/or transmitting.

The terms "transmit" and "transmitting" (and variations thereof) are meant to include standard means of provision of data, information, commands, signals, and/or instructions, but can also be used for non-traditional provisions as long as the data, information, commands, signals, and/or instructions is "sent." The terms "receive" and "receiving" (and variations thereof) are meant to include standard means of reception of data, information, commands, signals, and/or instructions, but can also be used for non-traditional methods of obtaining as long as the data, information, commands, signals, and/or instructions is "obtained."

Unless specifically stated otherwise, terms such as "first" and "second" are meant solely for purposes of designation and not for order or limitation. For example, the "first servo motor controller" has no order relationship with the "second servo motor controller." It should be noted that the terms "may," "might," "can," and "could" are used to indicate alternatives and optional features and only should be construed as a limitation if specifically included in the claims. It should be noted that the various components, features, steps, or embodiments thereof are all "preferred" whether or not it is specifically indicated. Claims not including a specific limitation should not be construed to include that limitation.

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A, B, A and B, or any combination thereof, but it would not have to include all of these possibilities). It should be noted that, unless otherwise specified, the terms "including" and "having" mean "comprising" (e.g. a device that includes, has, or comprises A and B contains A and B but optionally may contain C or additional components other than A and B). It should be noted that, unless otherwise specified, the singular forms "a," "an," and "the" refer to one or more than one, unless the context clearly dictates otherwise.

Eye Image and Video Capture Systems:

Described herein are various preferred and/or exemplary eye image and video capture systems for capturing images and video of a patient's eye. Eye image and video capture systems are preferably configured to be operably coupled to a slit lamp for examining a patient's eye. Some preferred eye image and video capture systems include a computing system, an optics controller, an optics assembly, a camera, and a flash assembly. Although shown as separate components, some of these elements may be combined in a single component. For example, the optics controller may be part of the computing system or part of the optics assembly. Alternatively, some of the functionality may be divided into multiple components. For example, the display may be distinct from the computing system. The specific configurations shown and described herein are meant to be exemplary and are not meant to limit the scope of the invention.

In such eye image and video capture systems, the optics assembly is preferably configured to be functionally coupled to a magnification portion and an ocular portion of the slit lamp. The camera is preferably configured to be functionally coupled to the optics assembly. The optics assembly preferably includes at least one adjustable light control component that can transmit a portion of the light exiting the magnification portion of the slit lamp toward the camera. Such transmission results in the camera with a same or generally similar view of the patient's eye as can be seen via the ocular portion of the slit lamp. The optics assembly also preferably includes at least one electronic and/or electrical adjustment component (e.g. at least one servo motor) that adjusts the light control components according to optics controller commands issued by the computing system. The camera is preferably operably coupled to the flash assembly and can cause the flash assembly to actuate when the camera is capturing an image.

The computing system preferably includes and/or is associated with a software program (referred to herein as a "system controller" a "facility") that provides interfaces that can be used to cause the camera to capture images and/or video. The system controller can allow a user to select one of a plurality of regions of the eye to image, each of which has correlated preset values for the camera and/or the light control components of the optics assembly. When the user selects a region of the eye to image, the system controller can transmit to the optics controller commands for adjusting the light control components of the optics assembly according to the preset values. The optics controller receives such commands and, in turn, transmits commands for adjusting the light control component(s) to the electronic and/or electrical adjustment component(s) of the optics assembly. The system controller can also transmit camera controller commands for controlling the camera to the camera according to the preset values. When the system controller receives an instruction to capture an image or video (e.g. a camera actuating command), the system controller can transmit a corresponding command to the camera. The camera actuates the flash if necessary and also captures an image or video. The camera transmits the captured image or video to the system controller, which can display the captured image or video for user (or a doctor or medical personnel) to review and/or store the captured image or video for later review.

Certain details are set forth in the following description and in FIGS. 1-11 to facilitate a thorough understanding of various preferred eye image and video capture systems. Other details describing well-known aspects of image and video capture systems, however, are not set forth in the following disclosure so as to avoid unnecessarily obscuring the description of the various preferred eye image and video capture systems.

Many of the details, dimensions, angles, and other features shown in the figures are merely illustrative of particular preferred eye image and video capture systems. Accordingly, other preferred eye image and video capture systems can have other details, dimensions, angles, and features. In addition, further preferred eye image and video capture systems can be practiced without several of the details described below.

In the Figures, identical reference numbers identify identical, or at least generally similar, elements. To facilitate the discussion of any particular element, the most significant digit or digits of any reference number refer to the figure in which that element is first introduced. For example, element 100 is first introduced and discussed with reference to FIG. 1.

Eye Image and Video Capture Systems and Associated Methods

FIG. 1 is a block diagram illustrating a preferred exemplary eye image and video capture system 100. The eye image and video capture system 100 is configured to be operably coupled to a slit lamp (for example, a tower-type slit lamp, such as those manufactured and/or sold by entities such as Marco, Haag-Streit, and others, a Zeiss-type slit lamp, or other types of slit lamps). The eye image and video capture system 100 includes a computing system 105, an optics controller 160, an optics assembly 170, a camera 180, a flash assembly 190, and connectors 155a/b, 165, 175, 185, and 195. The eye image and video capture system 100 can also include components not illustrated in FIG. 1, such as other connectors (for example, wired or wireless connectors) facilitating connections between the components of the eye image and video capture system 100. For example, batteries of the camera 180 and of the flash assembly 190 could be replaced with power supplies and associated cabling to enable the camera 180 and the flash assembly 190 to be plugged into standard 120 volt alternating current outlets.

The computing system 105 includes a memory 110 (for example, random-access memory, flash memory, read-only memory, etc.) and a persistent storage device 145 (for example, a hard disk drive, flash memory, etc.). The memory 110 includes software 115 incorporating a software program for imaging eyes (referred to herein as a system controller 120 or facility 120). The memory also includes data 125 typically used by the system controller 120. While the system controller 120 and data 125 are stored in memory 110 while being used, those skilled in the art will appreciate that these items, or portions of them, may be transferred between memory 110 and the persistent storage device 145 for purposes of memory management, data integrity, and/or other purposes. The computing system 105 further includes one or more central processing units (CPU) 135 for executing programs, such as the system controller 120. The computing system 105 also includes a display 140, which can be a touch-sensitive (touchscreen) display, one or more input devices 130 (for example, a keyboard, a mouse, a foot-activated input device, etc.), and one or more data input/output devices 150 (for example, a serial output device such as Universal Serial Bus (USB) output device). In other eye image and video capture systems, the computing system 105 can also include other components not illustrated in FIG. 1, such as a network connection device for wired or wireless connection to a network, and a computer-readable medium drive for reading information or installing programs such as the system controller 120 from tangible computer-readable storage media (for example, a floppy disk, a CD-ROM, a DVD, a USB flash drive, and/or other tangible computer-readable storage media).

The computing system 105 is functionally connected via connectors 155a and 155b (which can be, for example, electrical connectors such as USB connectors) to an optics controller 160. The optics controller 160 is functionally connected via connector 165 (which can be, for example, an RJ-45 connector) to an optics assembly 170. The optics assembly 170 is functionally coupled to a camera 180 (physical coupling is not shown in FIG. 1) and is also functionally connected to the camera 180 (shown as connecting via a connector 175). The camera 180 is functionally connected to the computing system 105 via a connector 195 (which can be, for example a USB connector) and is also connected to a flash assembly 190 via a connector 185.

Figure 2:
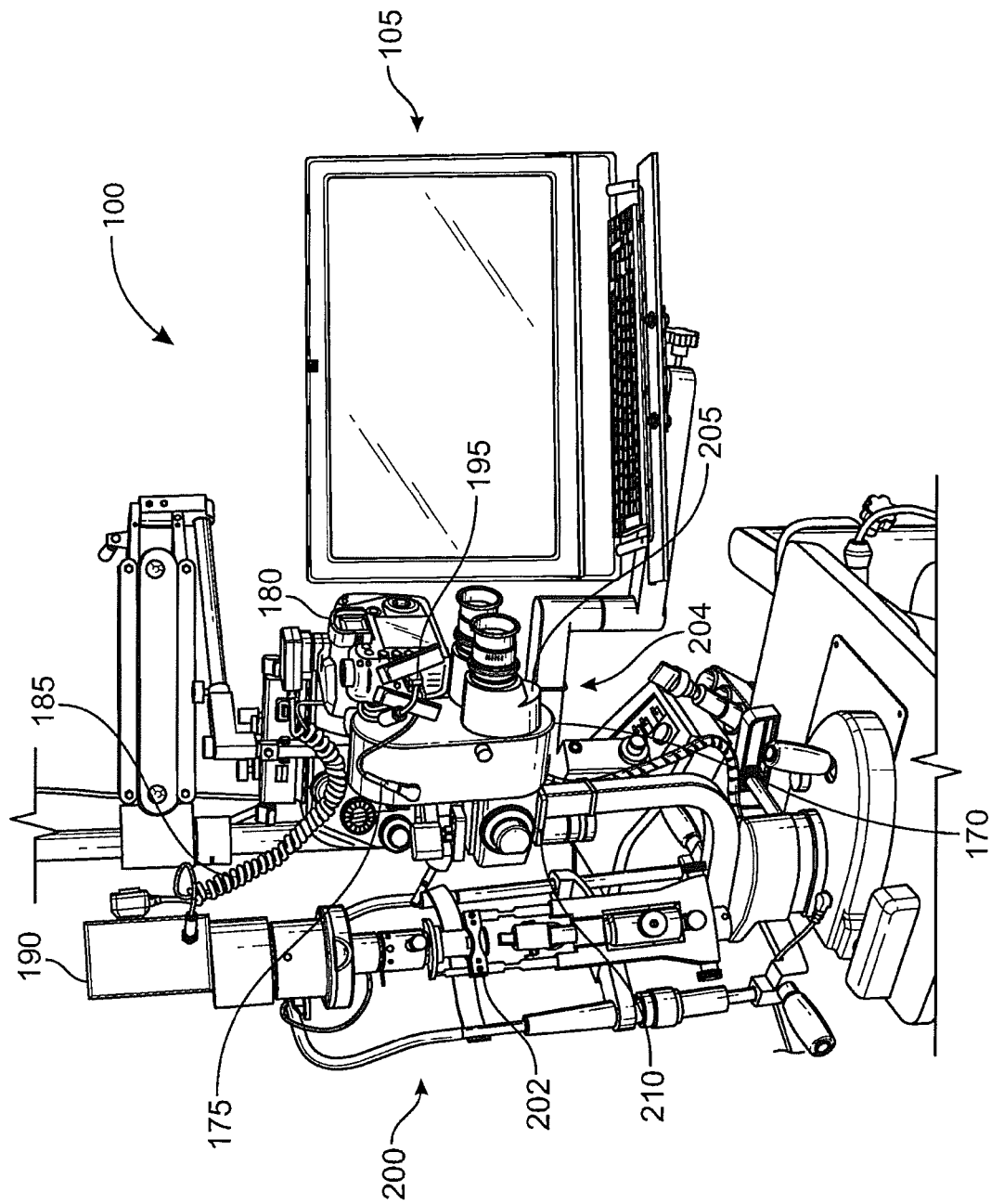
FIG. 2 is a schematic environmental image of portions of the eye image and video capture system of FIG. 1.

FIG. 2 shows how components of the eye image and video capture system 100 of FIG. 1 can be coupled to a slit lamp 200. The slit lamp 200 includes a light source portion 202 and a microscope portion 204. The light source portion 202 produces a slit of light that is shone into the eye of the patient being examined. The microscope portion 204 includes a magnification portion 210 and an ocular portion 205. Light enters the magnification portion 210 and is magnified by the magnification portion 210. This allows a user to see a magnified view of the patient's eye using the ocular portion 205.

As can be seen in FIG. 2, the optics assembly 170 can be functionally coupled to the slit lamp 200 between the magnification portion 210 and the ocular portion 205. FIG. 2 also shows how the camera 180 can be both functionally coupled to the optics assembly 170 and functionally connected to the optics assembly 170 via connector 175. Still further, FIG. 2 shows that the flash assembly 190 can be functionally coupled to the light source portion 202 and functionally connected (e.g. via the connector 185) to the camera 180 (for example, to a hot shoe connector of the camera 180). Finally, FIG. 2 shows the computing system 105 which, in the illustrated eye image and video capture system, includes a touchscreen display, a keyboard, and other components. An element that is not shown in FIG. 2 is a foot-activated input device that has at least one actuator (for example, for causing an image to be captured and/or for causing video to be captured).

Figure 3A:
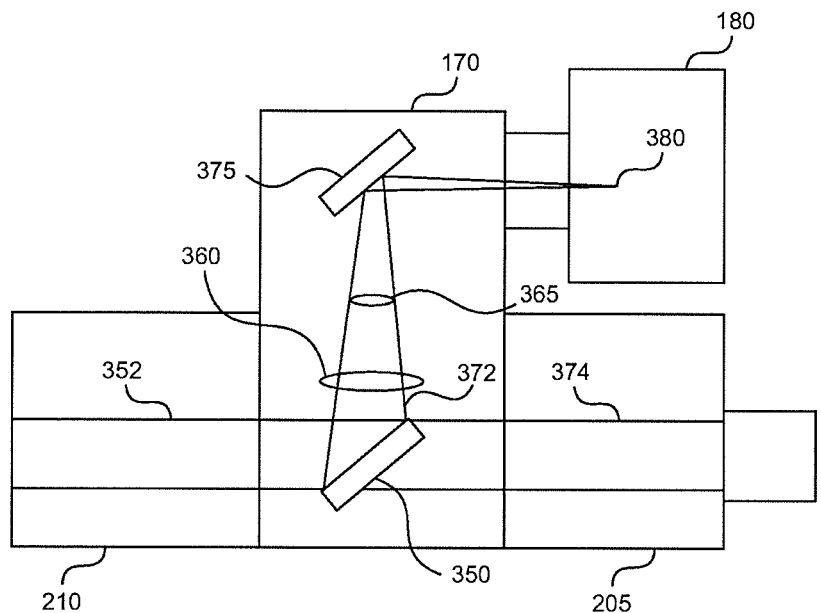
FIG. 3A is a block diagram illustrating components of an optics assembly and interfaces between the optics assembly, a camera, and a slit lamp of the eye image and video capture system of FIG. 1.

FIG. 3A is a block diagram illustrating paths of light through the magnification portion 210, the optics assembly 170 (shown as including a rotatable beam splitter 350 and a variable aperture 365), the ocular portion 205, and the camera 180. Light 352 travels through the magnification portion 210, exits the magnification portion 210, and travels into the optics assembly 170. The light 352 travels to the beam splitter 350 (for example, the beam splitter 350 can include a half-silvered mirror). The beam splitter 350 splits the light 352 and directs a first percentage of the light 352 (for example, from approximately 20 percent to approximately 60 percent) toward the ocular portion 205 (as indicated by reference number 374). The beam splitter 350 directs a second percentage of the light (for example, from approximately 40 percent to approximately 80 percent) towards the camera 180 (as indicated by reference number 372). As described in more detail herein, the beam splitter 350 may be rotatably movable by a first servo motor. Alternatively, the beam splitter may be stationary. The light 372 passes through a lens 360 (for example, a lens having a focal length of approximately 125 mm to approximately 200 mm) and then through a variable aperture 365.

Also as described in more detail herein, the variable aperture 365 is adjustable (the width of the aperture can vary) by a second servo motor. The light 372 is reflected one more time by a mirror 375 which correctly orients the image for the camera 180. The light 372 is focused by the lens onto a sensor of the camera 180 at a point 380. The distance between the lens 360 and the camera sensor is approximately equal to the focal length of the lens 360, thereby ensuring that the image or video captured by the camera sensor is in focus. To aid in fine focus control, the camera 180 is movable toward and away from the optics assembly 170 via a manual coupling (for example, a tube with threads). A user can adjust the manual coupling to move the camera 180 toward or away from the optics assembly 170 to ensure that the image or video captured by the camera 180 is properly focused.

In some preferred eye image and video capture systems, the camera 180 is functionally coupled to an upper horizontal surface of the optics assembly 170, such that the camera 180 is horizontally oriented (instead of vertically oriented as illustrated in FIG. 2). In such eye image and video capture systems, the optics assembly 170 does not include the mirror 375. Moreover, the lens 360 may be positioned differently or have a different focal length so as to ensure that the light 372 is properly focused onto the sensor of the camera 180.

Figure 3B:
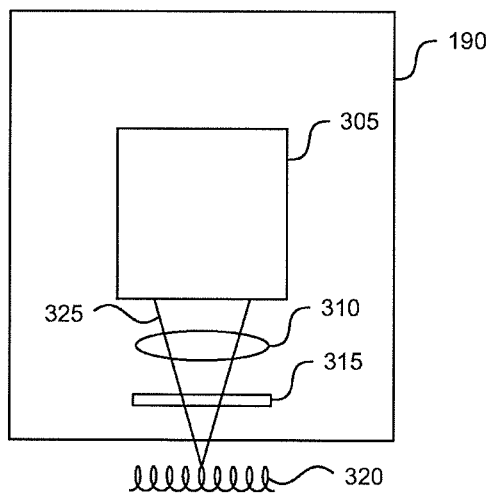
FIG. 3B is a block diagram illustrating components of a flash assembly of the eye image and video capture system of FIG. 1.

FIG. 3B is a block diagram illustrating components of the flash assembly 190. The flash assembly 190 includes a flash 305, which can be a standard external flash (for example, a standard external flash usable with the camera 180), a lens 310 (for example, a 90 diopter (90D) lens), and a hot mirror 315. The light source portion 202 of the slit lamp 200 includes a bulb having a filament (shown as filament 320 in FIG. 3B) that produces light that ultimately emerges as the slit of light that is shone into a patient's eye. When the flash 305 is activated, the flash 305 produces light 325 that is focused by the lens 310 onto the filament 320. The light is then transmitted via the light source portion 202 of the slit lamp 200 toward the eye of the patient being examined to momentarily increase illumination of the eye. The hot mirror 315 can be an infrared wavelength blocking lens that reflects infrared light away from the flash 305, thereby reducing any increase in temperature of the flash 305.

Figure 4:
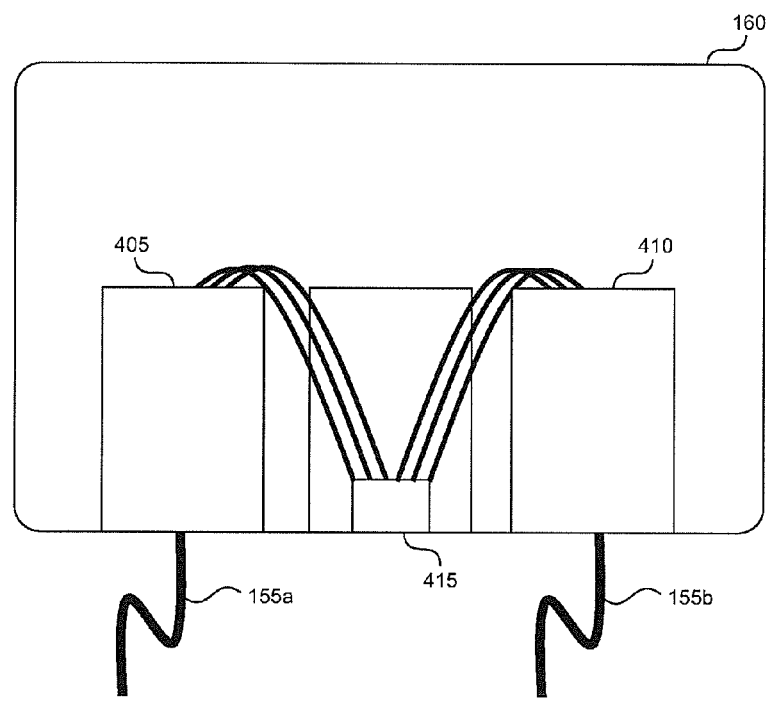
FIG. 4 is a partially schematic view illustrating components of an optics controller of the eye image and video capture system of FIG. 1.

FIG. 4 is a partially schematic view illustrating components of the optics controller 160. The shown optics controller 160 includes a first servo motor controller 405 for controlling a servo motor that rotates the beam splitter 350 (FIG. 3A). The shown optics controller 160 also includes a second servo motor controller 410 for controlling a servo motor that adjusts the variable aperture 365 (FIG. 3A). (It should be noted that alternative systems use only the first servo motor controller 405 for controlling a servo motor that rotates the rotatable beam splitter 350 or use only the second servo motor controller 410 for controlling a servo motor that adjusts the variable aperture 365. For example, the first servo motor would not be necessary if the beam splitter is fixed.) The first 405 and second 410 servo motor controllers are functionally connected to an input/output device 415 (for example, an RJ-45 jack). The first servo motor controller 405 is connected to the connector 155a and receives commands via the connector 155a from the computing system 105. The second servo motor controller 410 is connected to the connector 155b and receives commands via the connector 155b from the computing system 105. In some eye image and video capture systems, the first 405 and second 410 servo motor controllers are connected to the computing system 105 via at least one connector (for example, a USB connector).

Figure 5:
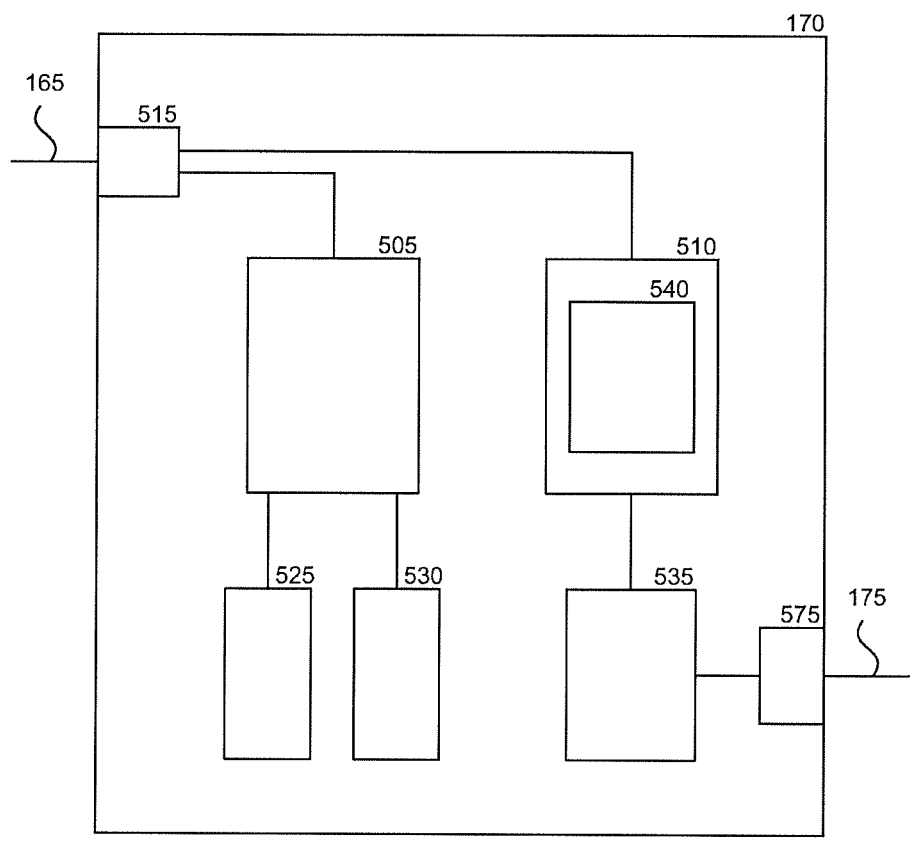
FIG. 5 is a block diagram illustrating additional components of the optics assembly of the eye image and video capture system of FIG. 1.

FIG. 5 is a block diagram illustrating components of the optics assembly 170. The optics assembly 170 includes an input/output device 515 (for example, an RJ-45 jack) to which the connector 165 is connected and a first circuit board 505 connected to the input/output device 515. The first circuit board 505 is functionally connected to a first servo motor 525 that rotatably moves the beam splitter 350 (for example, by rotating the beam splitter 350 about an axis of the beam splitter 350) and to a second servo motor 530 that adjusts the variable aperture 365 (for example, by rotating a gear to adjust the diameter width of the variable aperture 365). The first 525 and second 530 servo motors can be controlled using a pulse-width modulation (PWM) stream. For example, degrees of rotation of the first 525 and second 530 servo motors can be controlled according to the width of a pulse in the PWM stream.

In operation, the computing system 105 transmits commands to the first 405 and second 410 servo motor controllers. The first 405 and second 410 servo motor controllers, in turn, transmit commands via the connector 165 to the first 525 and second 530 servo motors to rotate the beam splitter 350 and to adjust the width of the variable aperture 365, respectively.

The optics assembly 170 also includes a second circuit board 510 connected to the input/output device 515. The second circuit board 510 includes a microcontroller 540. The optics assembly 170 also includes an optoisolator 535 connected to the second circuit board 510 and an input/output device 575. The input/output device 575 is connected via the connector 175 to a remote shutter control contact of the camera 180. (It should be noted that the first and second circuit boards 505, 510 may be implemented as a single circuit board or more than two circuit boards.)

Certain digital cameras have a "sleep mode," or "low-power mode," in which the camera is put into a low power state to conserve energy. Such cameras typically can be awakened from the "sleep mode" by pressing a power switch or otherwise activating the camera. One optional function of the microcontroller 540 is to transmit a signal to the camera 180 that "wakes up" the camera 180 if the camera 180 was in a "sleep mode." (This "wake up" feature is optional and would not be necessary if the camera does not have a "sleep mode." Further, a user may manually "wake" a sleeping camera.) As described in more detail herein, the system controller 120 of the computing system 105 can transmit a command to the optics controller 160 to wake up the camera 180. The second servo motor controller 410 receives the command and stops the PWM stream for the second servo motor 530 for a period of time. The microcontroller 540 monitors the signal from the second servo motor controller 410 and when the microcontroller 540 detects the absence of the PWM stream, the microcontroller 540 pulls an output pin high for 100 milliseconds. The output pin is connected to the optoisolator 535 which shorts its output stage. The output stage is connected via connector 175 to a ground pin and a half-press pin of the remote shutter control contact of the camera 180. The shorting of the ground pin and the half-press pin causes the camera 180 to wake up from sleep mode. In some preferred eye image and video capture systems, the functionality of the first 505 and second 510 circuit boards is implemented using at least one circuit board within the optics assembly 170.

Figure 6:
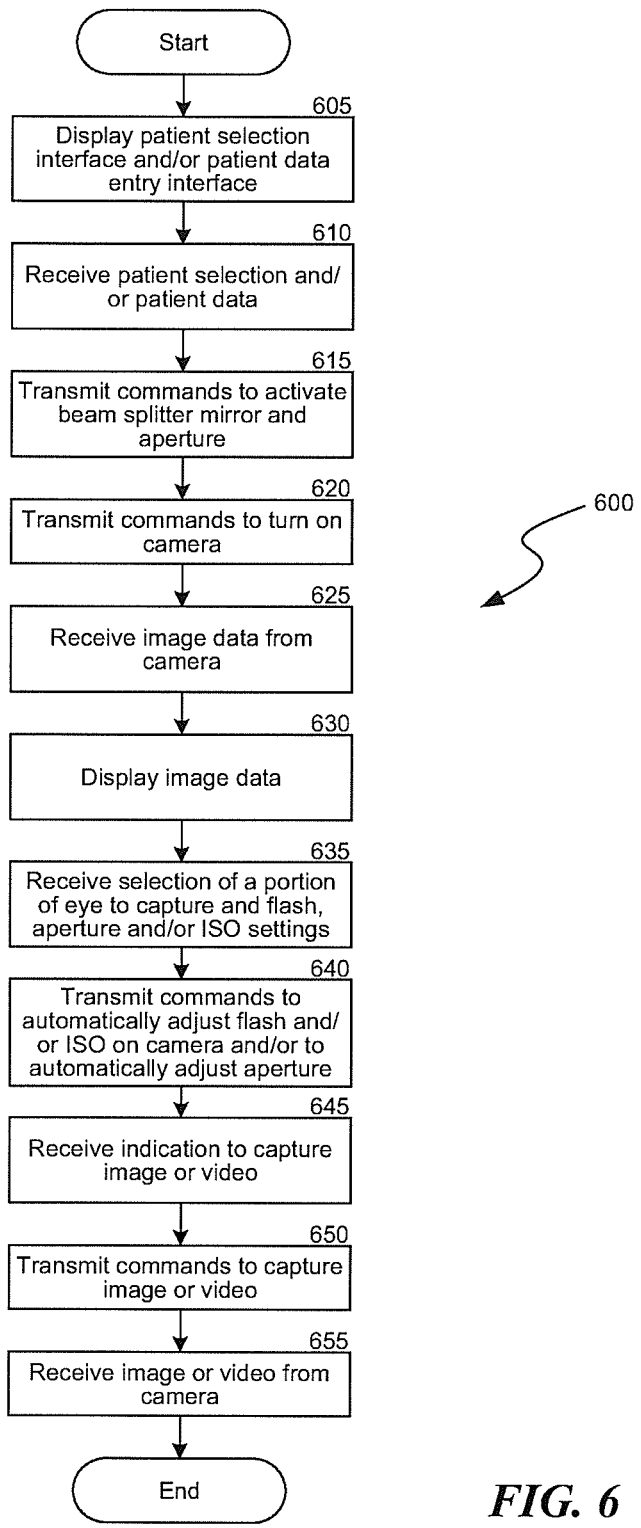
FIG. 6 is a flow diagram illustrating a process implemented by a system controller for imaging eyes in connection with capturing an image or video of an eye in accordance with a preferred eye image and video capture system.
Figure 7:
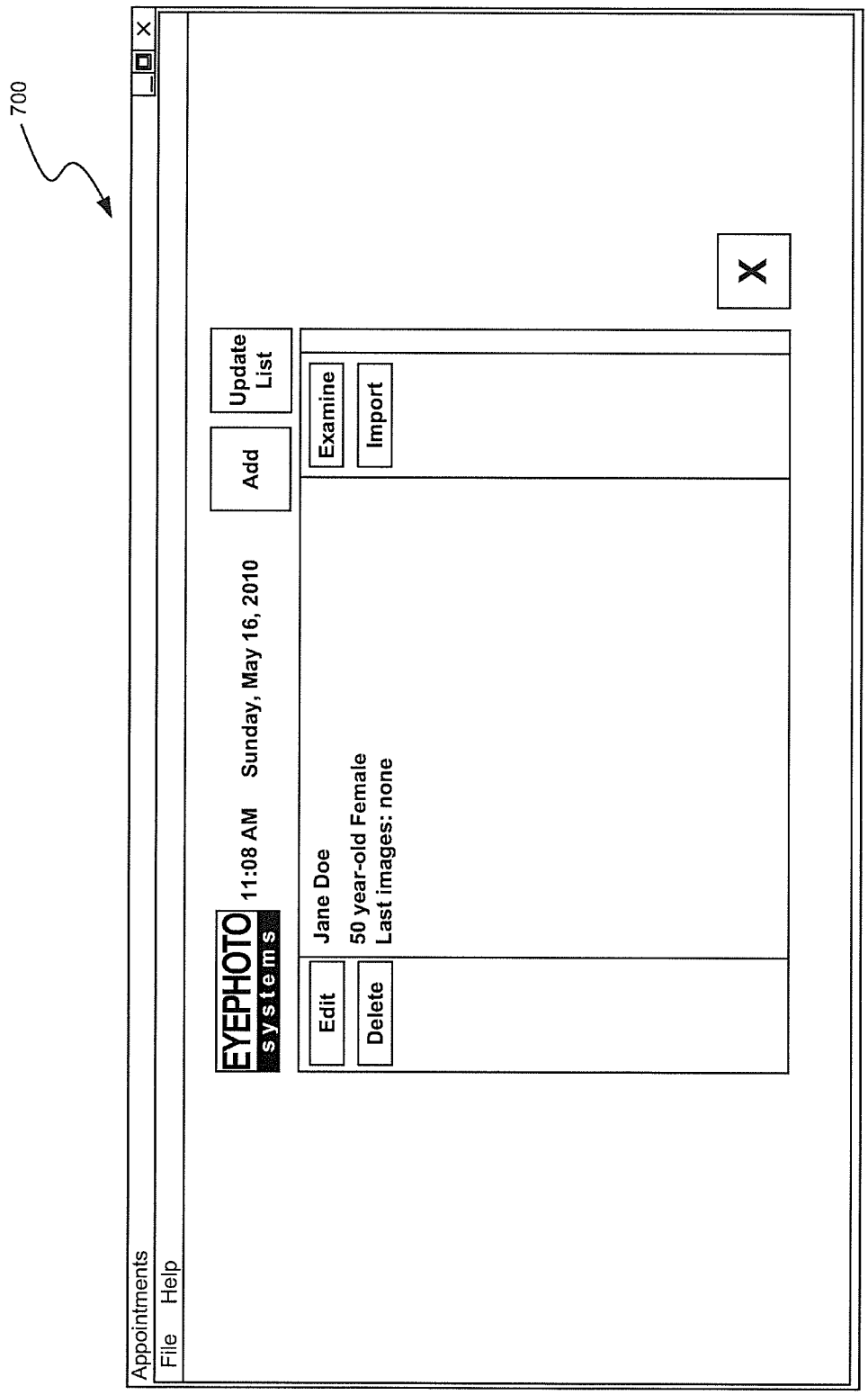
FIG. 7 is a display diagram illustrating a sample interface presented by the system controller in connection with receiving a selection of a patient in accordance with a preferred eye image and video capture system.
Figure 8:
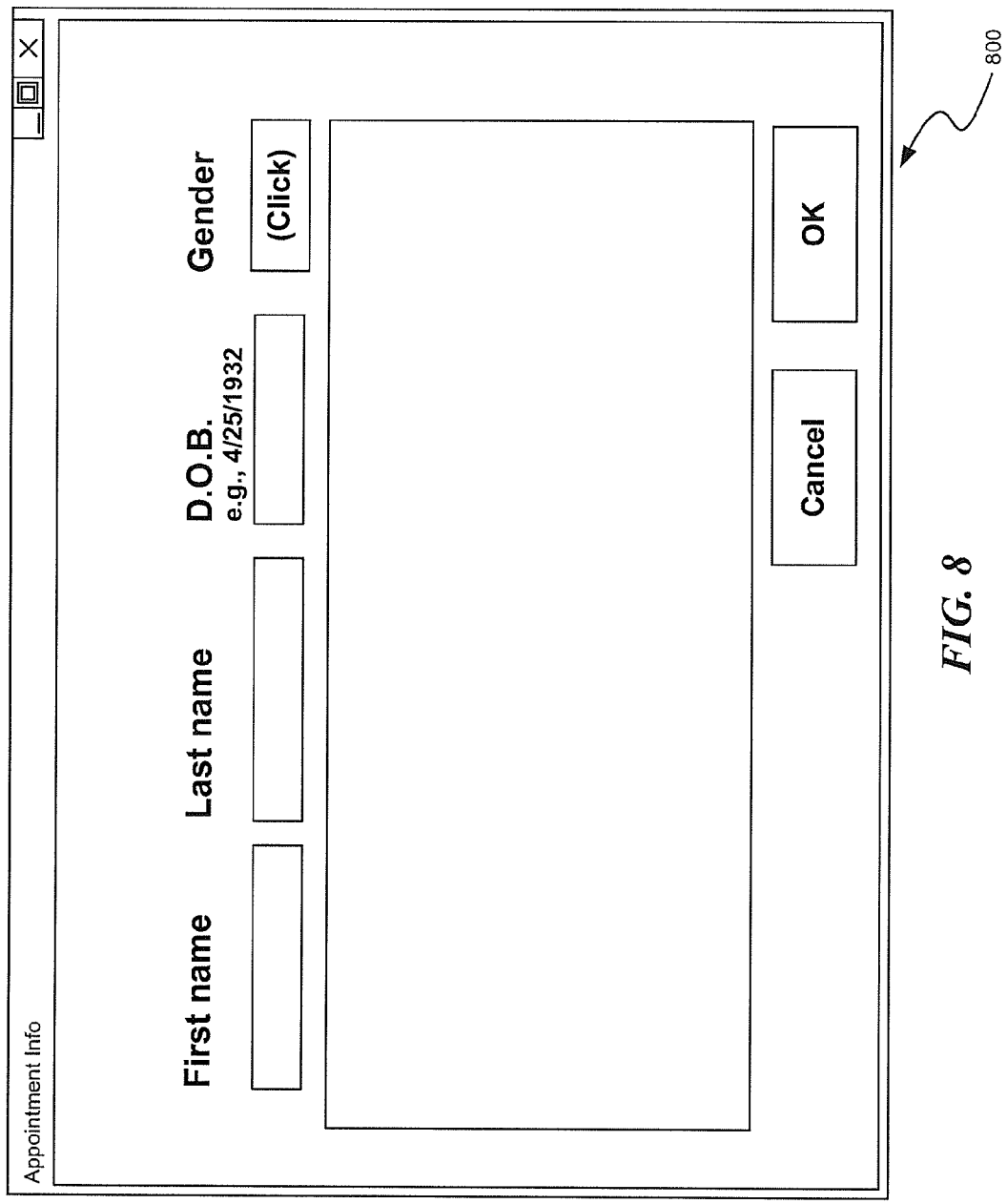
FIG. 8 is a display diagram illustrating a sample interface presented by the system controller in connection with receiving patient data in accordance with a preferred eye image and video capture system.

FIG. 6 is a flow diagram illustrating a process 600 implemented by the system controller 120 in connection with capturing images or video of an eye in some eye image and video capture systems. The process 600 begins at step 605 where the system controller 120 displays a patient selection interface and/or a patient data entry interface on the display 140. FIG. 7 is a display diagram illustrating an exemplary interface 700 presented by the system controller 120 in connection with receiving a selection of a patient. A user can select a patient (for example, using an input device 130) from a listing of patients and begin examining the patient by selecting a button labeled "Examine." The interface 700 also includes other buttons that allow the user to edit the patient's information, delete the patient from the listing, and import images from other sources for use by the system controller 120. For example, the system controller 120 can import images and video stored on the persistent storage device 145 or on other computing systems such that the system controller 120 can access the imported images and video. The user can select the button labeled "Add" to add a new patient. FIG. 8 is a display diagram illustrating a sample interface 800 presented by the system controller when the user selects the button labeled "Add." The user can enter patient data and select the button labeled "OK" to return to the interface 700 of FIG. 7.

Returning to FIG. 6, the process continues to step 610 where the system controller receives a selection of a patient (FIG. 7) and/or patient data (FIG. 8) and receives an instruction to begin an examination of the selected patient. At step 615, if the system includes a movable beam splitter 350, the system controller 120 transmits commands to activate the beam splitter 350. For example, prior to activation, the beam splitter 350 can be rotated out of position such that 100% of the light 352 exiting the magnification portion 210 of the slit lamp is sent to the ocular portion 205. Such positioning of the beam splitter 350 permits the user to examine the patient's eyes using light 374 that is 100% of the light 352 prior to the system controller 120 being activated for examination. The system controller 120 also transmits commands to activate the variable aperture 365. For example, prior to activation, the variable aperture 365 can be set to a minimum diameter, to a maximum diameter, or to a diameter therebetween, and the system controller 120 can transmit commands to adjust the variable aperture 365 to an appropriate width. At step 620 the system controller 120 transmits a command to prepare the camera 180 for use. The microcontroller 540 can then cause the camera 180 to wake up using the techniques described herein.

Figure 9:
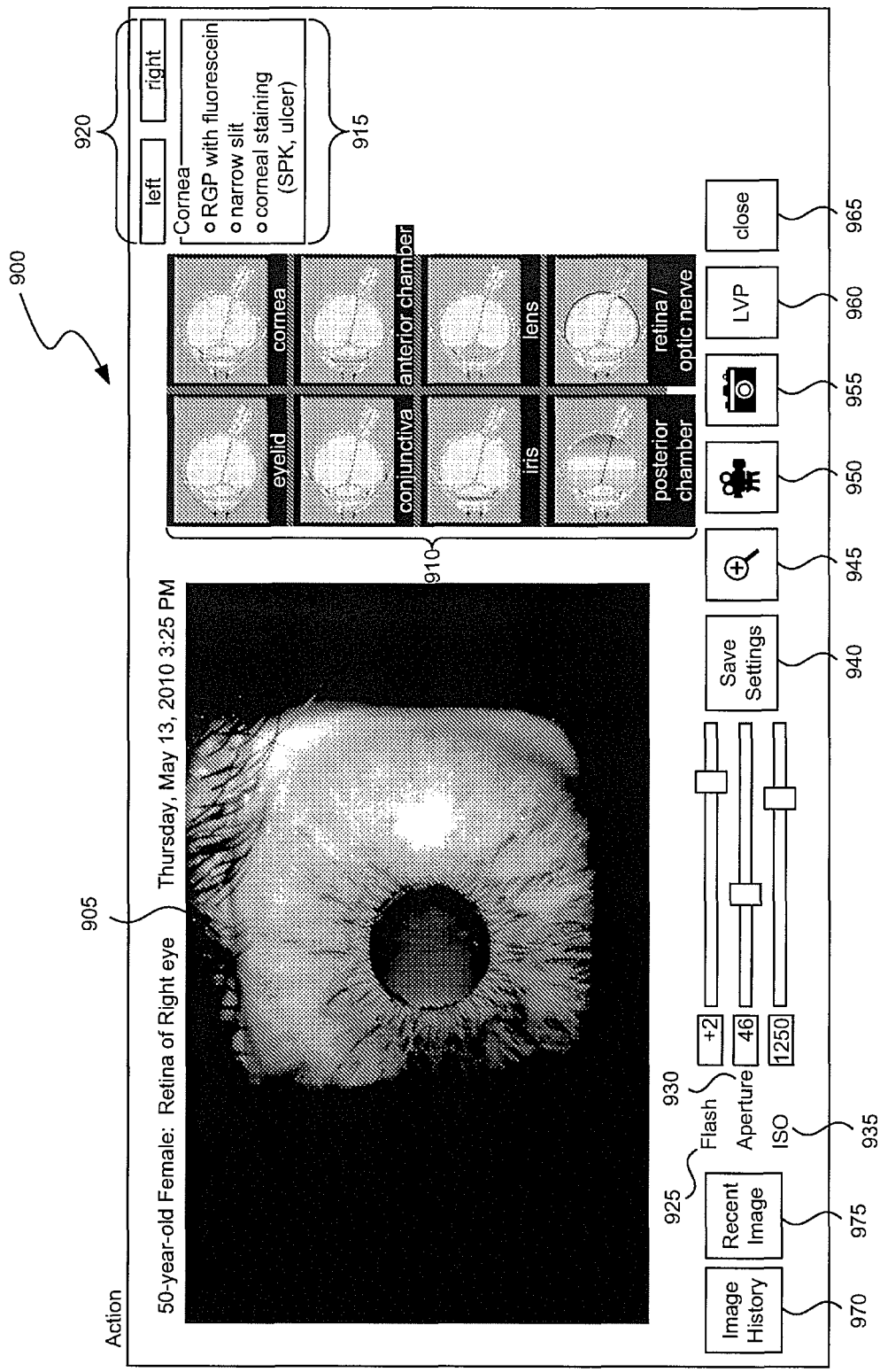
FIG. 9 is a display diagram illustrating a sample interface presented by the system controller in connection with receiving values and/or settings for imaging an eye and concurrently displaying real time eye image data in accordance with a preferred eye image and video capture system.

At step 625, the system controller 120 receives image data from the camera via the connector 195. At step 630 the system controller 120 displays the image data on the display 140. FIG. 9 is a display diagram showing a sample interface 900 presented by the system controller 120 in connection with receiving values for imaging an eye and concurrently displaying real time eye image data. The interface 900 includes a viewing section 905 for displaying real time eye image data received from the camera 180 in step 625. The shown interface 900 also includes exemplary control mechanisms such as "sliders" and "buttons" (e.g. selectable screen icons). The shown particular control mechanisms are meant to be exemplary and not meant to be limiting. For example, the interface 900 may include optional slider controls for providing the flash value 925, the aperture value 930, and/or the ISO value 935 to be used when imaging the patient's eye. As an exemplary alternative to sliders, a drop down menu could be used.

Using the control mechanism, the flash value 925 can be set from −3 (corresponding to a lowest intensity) to +3 (corresponding to a highest intensity) or turned off. The aperture value 930 can be set from 0 (corresponding to the variable aperture 365 being nearly closed—minimum diameter width) to 100 (corresponding to the variable aperture 365 being fully open—maximum diameter width). The ISO value 935 can be set from 6 to 6400. The flash value 925 and ISO value 935 can depend upon the make/model of the camera 180, and thus the ranges of allowable values for the flash 925 and ISO 935 settings can vary according to the camera 180 being used. The flash value 925 can depend upon the make/model of the flash assembly 190, and thus the ranges of allowable values for the flash setting 925 can vary according to the flash assembly 190 being used.

When the user sets the flash value 925 and ISO value 935, the system controller 120 transmits commands correlating to the values or settings to the camera 180 and the camera 180 is adjusted to the user-set values. When the user sets the aperture value 930, the system controller 120 transmits a command correlating to the value or setting to the optics controller 160. The optics controller 160, in turn, transmits a command to the second servo motor 410 that causes the variable aperture 365 to open or close according to the user-set value.

The interface 900 also includes a section 910 containing "buttons" corresponding to various regions of the eye that the user can select to have imaged. These regions include, for example, eyelid, cornea, conjunctiva, anterior chamber, iris, lens, posterior chamber, and retina/optic nerve. Each region of the eye has correlated with it a preset flash value 925, a preset aperture value 930, and a preset ISO value 935. When the user selects a region of the eye, the flash 925, the aperture 930, and the ISO 935 are set to the values correlated with the region, and the values are also transmitted to the camera 180 and/or the optics assembly 170. The system controller 120 thus allows the user to select a region of the eye to be imaged and to have the proper values set without additional direction from the user (e.g. "automatically") for the flash 925, the aperture 930, and the ISO 935. The user can manually adjust these preset values and select the button 940 labeled "Save Settings" to save the adjusted settings. The interface 900 also includes a section 920 allowing the user to manually specify which eye is being imaged (left or right) and a section 915 in which the user can specify additional information associated with the examination. The interface 900 also may include a control mechanism (shown as button 945) allowing the user to zoom in on a portion of the viewing section 905.

The preset values include, for example, the flash value 925, the aperture value 930, and the ISO value 935. (Additional preset values could include a zoom value, a video resolution value, a shutter speed value, and any other values that would affect the image and/or video.) The preset values may be based on data and/or formulas from the user and/or from the manufacturer. The preset values may be based on a combination of factors including, but not limited to, the specific region of the eye to image, the level of magnification, camera characteristics (e.g. the make/model of the camera 180), and/or flash assembly characteristics (e.g. the make/model of the flash assembly 190). The preset values may be data stored in table format in memory (e.g. memory 110) or may be calculated based on known formulas. An exemplary data table could be as follows:

| Magnification | Aperture |
| --- | --- |
| 10X | 8 |
| 16X | 6 |
| 25X | 4 |
| 40X | 3 |
| 6.3X | 11 |

Returning to FIG. 6, in step 635, the system controller 120 receives a selection of a region of the patient's eye to capture (for example, by receiving a selection of a button in section 910) and receives flash 925, aperture 930, and/or ISO 935 values or settings (as preset or as manually adjusted). In step 640, the system controller 120 transmits commands to adjust (without additional direction from the user) the flash and/or the ISO values on the camera 180 and/or commands to adjust (without additional direction from the user) the variable aperture 365 based on the selections received in step 635. In step 645, the system controller 120 receives an indication to capture image or video. For example, the user can select button 950 to begin capturing video (and select button 950 to stop capturing video) or button 955 to capture an image. As another example, the user can actuate a first button of a foot-activated input device to capture an image and a second button of the foot-activated input device to stop and start a video capture. In step 650, upon receiving the indication to capture image or video, the system controller 120 transmits the appropriate commands via the connector 195 to the camera 180. The camera 180 then captures an image or video according to the commands transmitted by the system controller 120. In step 655 the system controller 120 receives an image or video from the camera 180. The system controller 120 can then store the image or video (for example, on the persistent storage device 145). The system controller 120 directs the computing system 105 to display the image or video (or a frame of the video) in the viewing section 905 for a period of time. After step 655 the process 600 concludes.

Those skilled in the art will appreciate that the steps shown in FIG. 6 may be altered in a variety of ways. For example, the order of the steps may be rearranged, substeps may be performed in parallel, shown steps may be omitted, or other steps may be included. In reference to FIG. 6, it will be understood that each block of the flow chart, components of all or some of the blocks of the flow chart, and/or combinations of blocks of the flow chart, may be implemented by software (e.g. coding, software, computer program instructions, software programs, software subprograms, or other series of computer-executable or processor-executable instructions), by hardware (e.g. processors, memory), by firmware, and/or a combination of these forms. The blocks of the flow chart support combinations of steps, structures, and/or modules for performing the specified functions. It will also be understood that each block of the flow chart, and combinations of blocks in the flow chart, may be divided and/or joined with other blocks of the flow chart without affecting the scope of the invention. This may result, for example, in computer-readable program code being stored in whole on a single memory, or various components of computer-readable program code being stored on more than one memory.

Figure 10:
FIG. 10 is a display diagram illustrating a sample interface presented by the system controller in connection with displaying stored eye image data in accordance with a preferred eye image and video capture system.

Returning to FIG. 9, if the user wishes to further review the image or video or magnify a portion of the image or video, the user can select a button 975 labeled "Recent Image." Doing so causes the system controller 120 to provide (including generate and direct the display of) an interface allowing the user to review the most recent image or video captured. FIG. 10 is a display diagram illustrating a sample interface 1000 presented by the system controller 120 in connection with displaying the most recent image or video captured. If the display 140 is a touchscreen display, the user can press the touchscreen to magnify the image or video and/or to move to different sections of the image or video. The interface 1000 also includes buttons to allow the user to delete the image or video and to close the interface 1000 and return to the interface 900 of FIG. 9. If the user (or a doctor or other medical personnel) wishes to review several images of the patient's eyes, the user can simply select a button 970 labeled "Image History." Doing so causes the system controller 120 to display a gallery of images and/or video (stored, for example, on the persistent storage device 145) of the patient's eyes.

The interface 900 may also include a button 960 labeled "LVP," which stands for "Live View Priority." In some cases, certain regions of the eye are correlated with an aperture value 930 that is relatively small. If the user selects such a region, or if the user manually adjusts the aperture value 930 to be a low value, the image data displayed in viewing section 905 may not be of appropriate quality (for example, the image data may be too dark for a person viewing the viewing section 905). In such cases, the user can select the "LVP" button 960. Doing so causes the system controller 120 to transmit a command to open the variable aperture 365, thereby allowing more light to reach the camera 180. When the system controller 120 receives an indication to capture image or videos, the system controller 120 transmits a command to adjust the variable aperture 365 according to the preset aperture value 930 of the region of the eye the user wishes to image.

Preferred eye image and video capture systems 100 preferably have advantages that are significant to doctors and other users. Preferred eye image and video capture systems 100 include one or more of the following:

If the system controller 120 provides preset aperture, flash, and ISO values for certain regions of the eye that a user may wish to image, the system controller 120 can automatically configure the variable aperture 365 and the camera 180 according to the preset values correlated with the selected region of the eye. Using preset values and automatic configuration reduces or avoids the need for the user to manually adjust an aperture or a camera, thereby saving the user time and avoiding interruptions of the patient examination process.

If the system controller 120 provides the preset aperture, flash, and ISO values and automatically configuring aspects of the eye image and video capture system 100, the user does not need to become an expert in digital photography in order to properly capture image and video of a patient's eye. In some cases, the operation of the camera 180 can be completely hands-free (the user can capture images and video without touching the camera 180 during an examination session).

The automatic movement of the beam splitter 350 out of position when the system controller 120 is not being used ensures that 100% of the light reaches the ocular portion 205 of the slit lamp 200 when the system controller 120 is not being used.

The automatic "wake up" of the camera 180 if the camera 180 has gone into sleep mode or low power mode ensures that the camera 180 is ready to capture images or video when the user wishes to do so.

The user being able to capture both images and video using a camera, each of which is of high quality and in high resolution.

The eye image and video capture system 100 provides the same or generally similar view on the display 140 of the computing system 105 that can be seen using the ocular portion 205 of the slit lamp 200.

The eye image and video capture system 100 captures images or video that are the same or generally similar to what can be seen using the ocular portion 205 of the slit lamp 200.

Those of skill in the art will understand that the eye image and video capture system 100 has advantages other than those listed herein.

Slit Lamp Magnification Data Detection System:

A magnification portion 210 of a slit lamp 200 has an adjustable magnification control (for example, a knob or other movable component having a direct relation to the magnification data) that allows a user to adjust the magnification of light exiting the magnification portion 210 (for example, to certain settings such as six times magnification, 10 times magnification, 25 times magnification, etc.) The adjustable magnification control allows the user to magnify the view the user sees of a region of a patient's eye. Also, the system controller can use the magnification to select or adjust the preset values for the ISO, flash, and aperture.

In a system for capturing images or video of a patient's eye that is usable with a slit lamp, such as the eye image and video capture system 100 described herein, it can be desirable to automatically record the magnification data used when an image or video of a patient's eye is captured. For example, a computing system 105 can use the recorded magnification data and a captured image of a patient's eye to calculate a distance between two regions of an eye or to calculate an area of a region of an eye.

A conventional slit lamp, however, does not have a mechanism for automatically providing magnification data to a computing system or otherwise automatically recording the magnification data when an image or video of a patient's eye is captured. Furthermore, it may be undesirable to modify internal components of the adjustable magnification control since doing so may require special knowledge of the adjustable magnification control and may risk damaging the adjustable magnification control. Accordingly, it would be useful to have a system that 1) detects a slit lamp magnification setting (data) to use when an image or video is captured; 2) stores the magnification setting (data) in conjunction with (along with) the captured image or video; and 3) does not require undue modification of the adjustable magnification control.

Figure 11:
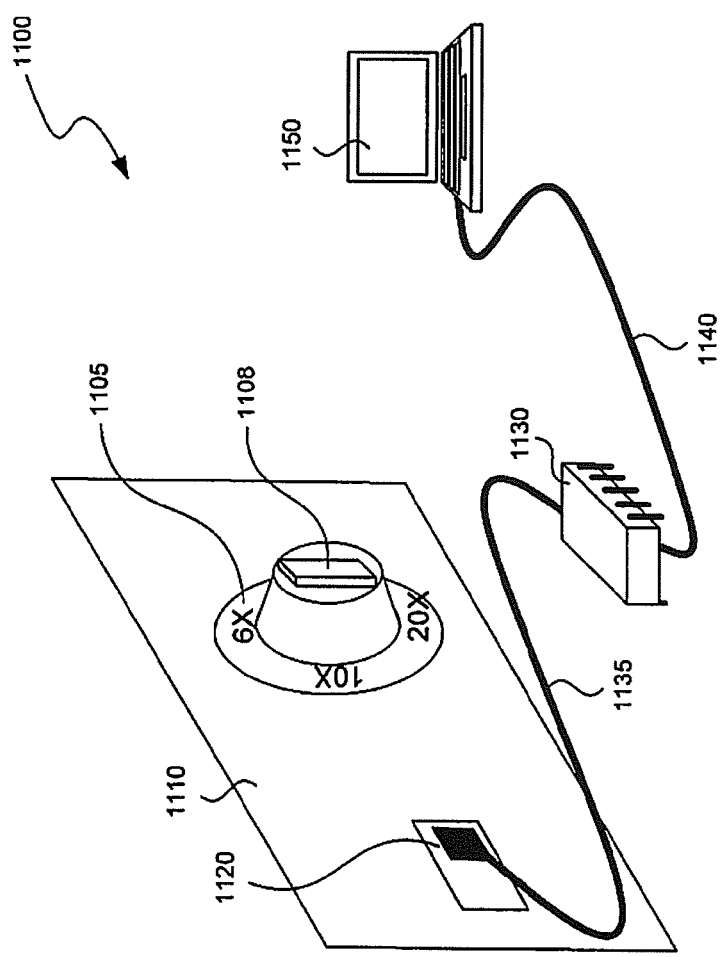
FIG. 11 is a partially schematic view of a slit lamp magnification data detection system configured in accordance with a preferred eye image and video capture system.

FIG. 11 is a partially schematic view of a slit lamp magnification data detection system 1100 configured in accordance with a preferred eye image and video capture system of the disclosure. The slit lamp magnification data detection system 1100 (also see 210) includes a magnet 1108 (the magnet 1108 generally representing a first part of a position indicator/detector system) affixed to an adjustable magnification control 1105 of a magnification portion 1110 of a slit lamp. The magnet 1108 can be, for example, a bar magnet that is magnetized along its length and can be affixed (for example, with tape, adhesive, or other suitable material) to a planar surface of the adjustable magnification control 1105. The slit lamp magnification detection system 1100 also includes a digital compass 1120 (the digital compass 1120 generally representing a second part of a position indicator/detector system) that is affixed (for example, with tape, adhesive, or other suitable material) to the magnification portion 1110 proximate to the adjustable magnification control 1105. For example, the digital compass 1120 may be positioned anywhere from approximately one inch away to approximately five or more inches away from the adjustable magnification control 1105. The shown positions of the two parts of the indicator/detector system are meant to be exemplary as other positions are contemplated.

The digital compass 1120 has a measurement plane and is positioned such that the measurement plane is perpendicular to an axis of rotation of the adjustable magnification control 1105. The digital compass 1120 has power leads (not illustrated in FIG. 11) that are connected to a suitable power supply (for example, 5 Volts direct current, not illustrated in FIG. 11). The slit lamp magnification detection system 1100 also includes a microcontroller 1130 functionally connected to signal leads of the digital compass 1120 via a connector 1135. The microcontroller 1130 is, in turn, functionally connected via a connector 1140 (for example, a USB connector) to a computing system 1150. The microcontroller 1130 executes software and/or firmware that controls the digital compass 1120 and communicates with the computing system 1150.

During installation of the slit lamp magnification data detection system 1100, the digital compass 1120 may be calibrated. For example, an installer can calibrate the digital compass 1120 to account for interfering magnetic fields from sources other than the magnet 1108. After calibration, the installer can index magnification settings of the adjustable magnification control 1105 to readings of the digital compass 1120. For example, the installer can adjust the adjustable magnification control 1105 to a specific setting, such as six times magnification, and provide the setting to the computing system 1150. The microcontroller 1130 can concurrently receive a signal from the digital compass 1120 indicating a position (compass angle) of the digital compass 1120. The microcontroller provides an indication of the digital compass position to the computing system 1150. The computing system 1150 stores the magnification setting in conjunction with (along with) the digital compass position. The installer can repeat the aforementioned steps for each magnification setting, such that each magnification setting is stored in conjunction with (along with) a digital compass position. For example, the computing system 1150 can store the magnification settings and the digital compass positions in a look-up table indexed by digital compass position, or using any other suitable data structure.

Put another way, the position indicator/detector system (including, for example, the magnet 1108 and the digital compass 1120) is able to gauge the relationship between its first part and its second part (e.g. the position or compass angle). The position indicator/detector system is also able to receive commands from and to transmit data (e.g. signals related to the position or compass angle) to the system controller. There is a direct relation between the position of the movable component (e.g. the adjustable magnification control 1105) and the slit lamp magnification data. One part of the position indicator/detector system is attached to the movable component. The other part of the position indicator/detector system is attached to a stationary component (that may be part of the slit lamp or positioned substantially near thereto). Because the position indicator/detector system is able to gauge the relationship (e.g. distance and/or angle) between its parts, the position indicator/detector system is able to provide meaningful relationship data to the system controller so that the system controller can determine (which specifically includes calculate and look-up) the slit lamp magnification data based on the relationship between the movable and stationary components to which the parts of the system controller are attached.

During a patient examination, the digital compass 1120 can provide a signal indicating a position of the digital compass 1120 to the microcontroller 1130, which can provide an indication of the digital compass position to the computing system 1150. The computing system 1150 receives the digital compass position indication and accesses the stored correlations between magnification settings and digital compass positions to determine the magnification setting corresponding to the digital compass indication. The computing system 1150 can thus determine the magnification setting of the adjustable magnification control 1105 and thus the magnification used by the slit lamp. In a system for capturing images or video of a patient's eye, the system can store the magnification data used when an image or video is captured in conjunction with (along with) the captured image or video.

It will be appreciated that other methods to affix the magnet 1108 to the adjustable magnification control 1105 and to affix the digital compass 1120 to the magnification portion 1110 may be utilized. It will be further appreciated that the adjustable magnification control 1105 could be rotatable around two or more axes and that a three-axis digital compass could be used to determine an orientation of the adjustable magnification control 1105 and thus a corresponding magnification. It will be further appreciated that a slit lamp magnification data detection system may utilize other sensors to sense a magnification setting of the magnification portion 1110 of the slit lamp, such that a magnification used when an image or video of a patient's eye is captured can be stored in conjunction with (along with) the captured image or video. Still further, the slit lamp magnification data detection system can be incorporated into new systems and/or retrofitted into existing systems.

Slit Lamp Position Data Detection System:

In a system for capturing images or video of a patient's eye that is usable with a slit lamp, such as the eye image and video capture system 100 described herein, it can be desirable to automatically record which eye has been imaged (data). For example, a computing system can store an indication of which eye has been imaged in conjunction with (along with) the captured image or video of the eye. A doctor can utilize the stored indication (data) for diagnostic purposes. Accordingly, it would be useful to have a system that automatically records an indication of which eye has been imaged (data).

Figure 12:
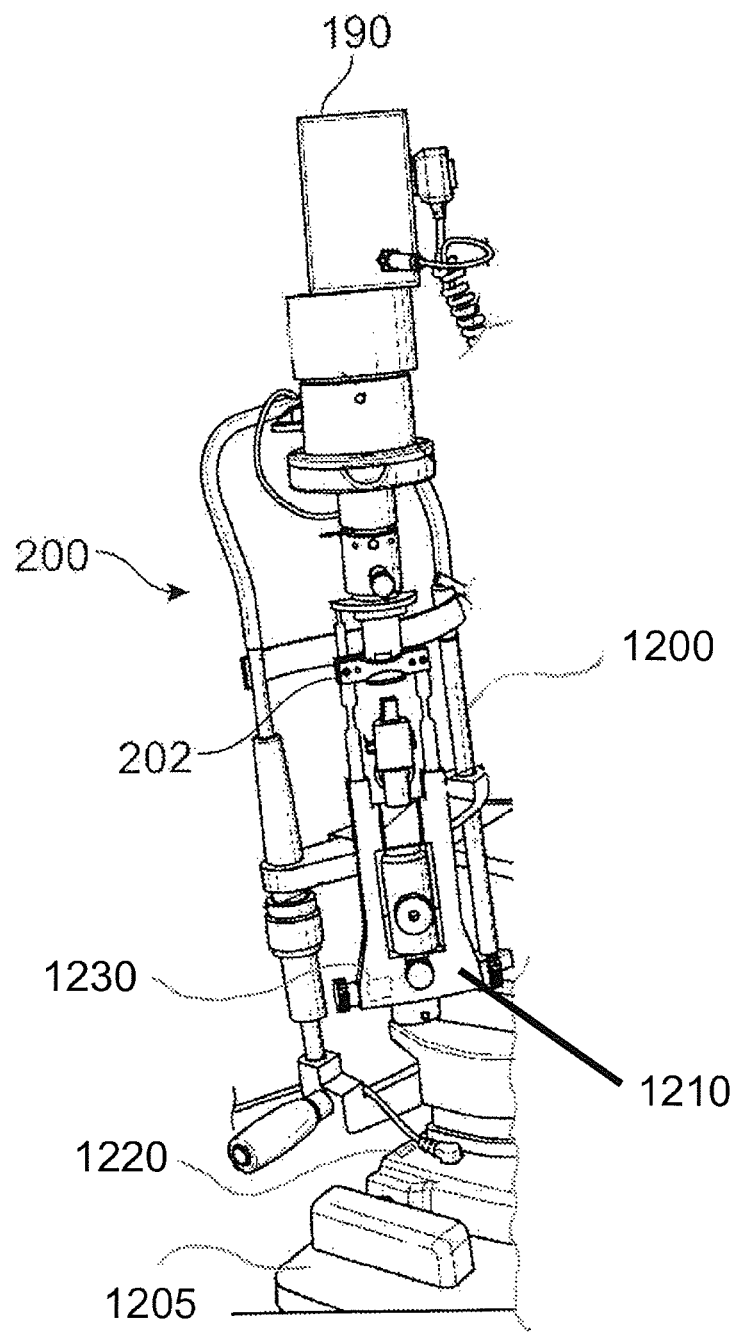
FIG. 12 is a perspective view of a slit lamp position data detection system configured in accordance with a preferred eye image and video capture system.

As shown in FIG. 12, typical slit lamps include a patient interface portion 1200 against which the patient's head is positioned during an examination. The patient interface portion 1200 is functionally coupled to a stationary base 1205 and is not movable with respect to the stationary base 1205. The slit lamp also includes one or more movable portions 1210 (for example, portions of the optical assembly such as the light source portion 202, the magnification portion 210, and/or the ocular portion 205 illustrated in FIG. 2) that are laterally movable with respect to the stationary base 1205 and thus to the patient interface portion 1200. The ability to laterally move the magnification and ocular portions of the slit lamp allows a doctor to examine both the left and the right eyes of the patient. The movable portion or component has a direct relation to which eye has been imaged (data)

In some preferred eye image and video capture systems, a slit lamp position data detection system includes a magnet 1220 (the magnet 1220 generally representing a first part of a position indicator/detector system) affixed to a stationary portion of a slit lamp (for example, a slit lamp base 1205) and a digital compass 1230 (the digital compass 1230 generally representing a second part of a position indicator/detector system) affixed to a movable portion 1210 of the slit lamp that is laterally movable with respect to the stationary portion of the slit lamp. The shown positions of the two parts of the indicator/detector system are meant to be exemplary as other positions are contemplated. The slit lamp position detection system can also include components similar to the slit lamp magnification detection system 1100 of FIG. 11, such as a microcontroller connected to the digital compass and to a computing system.

In some preferred eye image and video capture systems, the position indicator/detector system includes an optical reflectometer (such as the QRD1114 reflectance sensor) and a target (that may be a dark colored sticker that is less reflective than tables upon which the system will be positioned). The reflectometer may be connected to either the movable component (e.g. the optics assembly) or the stationary component (e.g. a table, a stationary base, or the patient interface portion). The target is attached to the opposite component. The reflectometer measures the reflectance of a material by emitting light (for example, from a light emitting diode) and measuring the light level that is reflected back by the target material (for example, by using a phototransistor to convert light level to a voltage level). When the movable component is moved to the left (that is, when the user is examining the patient's right eye), the reflectometer may be positioned over the highly reflective, light-colored table top (without the target) and it senses more light being reflected. Conversely, when the movable component is moved to the right, the reflectometer is positioned over the less reflective, dark-colored sticker (the target) and it senses less light being reflected. The system controller periodically transmits a command to the optics assembly causing the optics assembly to transmit the current light level from reflectometer back to the system controller. With that information, the system controller infers which eye is being examined and includes that information in any captured images or videos.

During installation of the slit lamp position detection system, the digital compass 1230 may be calibrated. For example, an installer can calibrate the digital compass to account for interfering magnetic fields from sources other than the magnet. After calibration, the installer can index left eye and right eye position settings to readings of the digital compass. For example, the installer can adjust the position of the movable portion of the slit lamp such that it corresponds to a position used for examining a patient's left eye. The microcontroller can concurrently receive a signal from the digital compass indicating a position (compass angle) of the digital compass. The microcontroller provides an indication of the digital compass position to the computing system. The computing system stores an indication that the digital compass position corresponds to the left eye. The installer can repeat the aforementioned steps for finding a position corresponding to an orientation used for examining a patient's right eye. For example, the computing system can store the digital compass position and the left eye and right eye indications in a look-up table indexed by digital compass position, or using any other suitable data structure.

Put another way, the position indicator/detector system (including, for example, the magnet 1220 and the digital compass 1230 or, alternatively, the optical reflectometer and its associated target) is able to gauge the relationship between its first part and its second part (e.g. the position or compass angle or, alternatively, the position based on the presence or absence of the target (also referred to as the presence/absence relationship)). The position indicator/detector system is also able to receive commands from and to transmit data (e.g. signals related to the position or compass angle) to the system controller. There is a direct relation between the position of the movable component 1210 (e.g. portions of the optical assembly) and the slit lamp position data. One part of the position indicator/detector system is attached to the movable component. The other part of the position indicator/detector system is attached to a stationary component (that may be part of the slit lamp or positioned substantially near thereto). Because the position indicator/detector system is able to gauge the relationship (e.g. distance, angle, and/or presence or absence) between its parts, the position indicator/detector system is able to provide meaningful relationship data to the system controller so that the system controller can determine (which specifically includes calculate and look-up) the slit lamp position data based on the relationship between the movable and stationary components to which the parts of the system controller are attached.

During a patient examination, the digital compass can provide a signal indicating a position of the digital compass (data) to the microcontroller, which can provide an indication of the digital compass position (data) to the computing system. The computing system receives the digital compass position indication and accesses the stored correlations between a left eye or a right eye and the digital compass positions to determine whether it is the left eye or the right eye being examined. In a system for capturing images or video of a patient's eye, when an image or video is captured of the patient's eye, the system can thus automatically store an indication of which eye has been imaged (data) in conjunction with (along with) the captured image or video.

It will be appreciated that other means and methods may be used to affix the magnet 1210 and the digital compass 1220. It will be further appreciated that a slit lamp position data detection system may utilize other sensors to sense a position setting, such that an indication of which eye has been imaged can be stored in conjunction with (along with) the captured image or video. Still further, the slit lamp position data detection system can be incorporated into new systems and/or retrofitted into existing systems.

From the foregoing, it will be appreciated that specific, representative, preferred eye image and video capture systems have been described herein for purposes of illustration, but that various modifications may be made to these preferred eye image and video capture systems. For example, the optics controller 160 could be incorporated into the computing system 105 or into the optics assembly 170. As another example, the camera 180 could receive commands for "waking up" from sleep mode from the system controller 120 via the connector 195 instead of via the connector 175. In such an example, the camera 180 is not electrically coupled to the optics assembly 170. Additional preferred eye image and video capture systems are within the scope of the present disclosure. For example, methods of manufacturing and/or assembling eye image and video capture systems in accordance with preferred eye image and video capture systems described herein are within the scope of the present disclosure. Further, while advantages relating to certain preferred eye image and video capture systems have been described in the context of those eye image and video capture systems, other eye image and video capture systems may also exhibit such advantages, and not all eye image and video capture systems need necessarily exhibit such advantages to fall within the scope of the present disclosure.

The terms and expressions that have been employed in the foregoing specification are used as terms of description and not of limitation, and are not intended to exclude equivalents of the features shown and described. While the above is a complete description of selected embodiments of the present invention, it is possible to practice the invention use various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall therebetween.

What is claimed is:

1. An eye image and video capture system comprising a computing system, an optics controller, an optics assembly having at least one adjustable light control component, a camera, and a flash assembly, said computing system having a system controller having a series of instructions that cause the system to:
   (a) provide at least one user interface from which a user may select one from a list of a plurality of distinct anatomical regions of an eye to image, the list comprising at least two of eyelid, cornea, conjunctiva, anterior chamber, iris, lens, posterior chamber, and optic nerve, each of said plurality of regions having at least one correlated preset value for the light control components of the optics assembly, each of said plurality of regions having at least one correlated preset value for controlling the camera;
   (b) provide at least one user interface from which a user may select to cause the camera to selectively capture at least one image or capture at least one video;
   (c) receive a user selection of one of said plurality of regions of an eye to image from the list of such regions;
   (d) receive a user selection of either causing the camera to capture at least one image or causing the camera to capture at least one video;
   (e) transmit at least one optics controller command for adjusting the at least one adjustable light control component of the optics assembly according to the at least one preset value correlated with said user selection of one of said plurality of regions of an eye to image;
   (f) transmit at least one camera controller command for controlling the camera according to the at least one preset value correlated with said user selection of one of said plurality of regions of an eye to image; and
   (g) transmit at least one camera actuating command for controlling the camera according to said user selection of one of said causing the camera to capture at least one image or causing the camera to capture at least one video.

2. A method for capturing an image or a video using an eye image and video capture system, said eye image and video capture system comprising a computing system, an optics controller, an optics assembly having at least one adjustable light control component, a camera, and a flash assembly, said method comprising the steps of:
   (a) providing at least one user interface from which a user may select one from a list of a plurality of distinct anatomical regions of an eye to image, the list comprising at least two of eyelid, cornea, conjunctiva, anterior chamber, iris, lens, posterior chamber, and optic nerve, each of said plurality of regions having at least one correlated preset value for the light control components of the optics assembly, each of said plurality of regions having at least one correlated preset value for controlling the camera;
   (b) providing at least one user interface from which a user may select to cause the camera to selectively capture at least one image or capture at least one video;
   (c) receiving a user selection of one of said plurality of regions of an eye to image from the list of such regions presented to the user;
   (d) receiving a user selection of either causing the camera to capture at least one image or causing the camera to capture at least one video;
   (e) transmitting commands for adjusting the at least one adjustable light control component of the optics assembly according to the at least one preset value correlated with said user selection of one of said plurality of regions of an eye to image;
   (f) transmitting commands for controlling the camera according to the at least one preset value correlated with said user selection of one of said plurality of regions of an eye to image; and
   (g) transmitting commands for controlling the camera according to said user selection of one of said causing the camera to capture at least one image or causing the camera to capture at least one video.

3. The system of claim 1, said computing system having at least one memory, said system controller stored on said at least one memory.

4. The system of claim 1, said computing system having at least one processing unit, said at least one processing unit executing said series of instructions.

5. The system of claim 1, said system controller having a series of instructions that cause the system to transmit the optics controller commands for adjusting the at least one adjustable light control component according to the at least one preset value correlated with said user selection of one of said plurality of regions of an eye to image via the optics controller to the at least one adjustable light control component.

6. The system of claim 1, said system controller having a series of instructions that cause the system to transmit the optics controller commands for adjusting the at least one adjustable light control component according to the at least one preset value correlated with said user selection of one of said plurality of regions of an eye to image via the optics controller, the optics controller receiving the optics controller commands from the system, the optics controller transmitting commands to the at least one adjustable light control component.

7. The system of claim 1, said system controller having at least one instruction that causes the system to transmit commands for actuating a flash.

8. The system of claim 1, said system controller having at least one instruction that causes the system to transmit commands via said camera for actuating a flash.

9. The system of claim 1, said system controller having at least one instruction that causes the system to receive at least one captured image from the camera.

10. The system of claim 1, said system controller having at least one instruction that causes the system to receive at least one captured video from the camera.

11. The system of claim 1, wherein the camera controller command includes at least one value selected from a group comprising a flash power setting, an ISO value, a video resolution value, a white-balance setting, an auto-exposure setting, and a shutter speed value.

12. The method of claim 2 further comprising a step of controlling said steps using a system controller stored in memory of said computing system.

13. The method of claim 2 further comprising a step of executing said steps using a processing unit of said computing system.

14. The method of claim 2 further comprising a step of transmitting the optics controller commands for adjusting the at least one adjustable light control component according to the at least one preset value correlated with said user selection of one of said plurality of regions of an eye to image via the optics controller to the at least one adjustable light control component.

15. The method of claim 2 further comprising a step of transmitting the optics controller commands for adjusting the at least one adjustable light control component according to the at least one preset value correlated with said user selection of one of said plurality of regions of an eye to image via the optics controller, the optics controller receiving the optics controller commands from the system, the optics controller transmitting commands to the at least one adjustable light control component.

16. The method of claim 2 further comprising a step of transmitting commands for actuating a flash.

17. The method of claim 2 further comprising a step of transmitting commands via said camera for actuating a flash.

18. The method of claim 2 further comprising a step of receiving at least one captured image from the camera.

19. The method of claim 2 further comprising a step of receiving at least one captured video from the camera.

20. The system of claim 9, said system controller having at least one instruction that causes the system to display said at least one captured image.

21. The system of claim 10, said system controller having at least one instruction that causes the system to display said at least one captured video.

22. The system of claim 11, wherein the camera controller command includes at least one of a flash power setting, a shutter speed value, and an ISO value.

23. The method of claim 18 further comprising a step of displaying said at least one captured image.

24. The method of claim 19 further comprising a step of displaying said at least one captured video.

25. The system of claim 22, wherein the camera controller command includes a command selected from a group of multiple commands comprising a flash command, an aperture setting, or an ISO value.

\* \* \* \* \*